United States Patent
Reith et al.

(10) Patent No.: US 8,169,622 B1
(45) Date of Patent: May 1, 2012

(54) OPTICAL SENSOR FOR MOUNTING TO A WASHING MACHINE OR DISH WASHER

(75) Inventors: Andreas Reith, Bogen (DE); Martin Brabec, Nabburg (DE); Johann Schenkl, Bodenwoehr (DE)

(73) Assignee: emz-Hanauer GmbH & Co. KGaA, Nabburg (DE)

( * ) Notice: Subject to any disclaimer, the term of this patent is extended or adjusted under 35 U.S.C. 154(b) by 0 days.

(21) Appl. No.: 12/940,185

(22) Filed: Nov. 5, 2010

(51) Int. Cl.
*G01B 11/24* (2006.01)
(52) U.S. Cl. ........ 356/601; 200/511; 200/512; 356/442; 356/445
(58) Field of Classification Search .......... 200/511–512; 356/442–445
See application file for complete search history.

(56) References Cited

U.S. PATENT DOCUMENTS

| | | | | |
|---|---|---|---|---|
| 5,589,935 | A * | 12/1996 | Biard | 356/339 |
| 7,733,097 | B2 * | 6/2010 | Schenkl et al. | 324/693 |
| 2007/0095643 | A1 * | 5/2007 | Weiss et al. | 200/511 |

FOREIGN PATENT DOCUMENTS

WO 2006050767 5/2006

* cited by examiner

*Primary Examiner* — Gregory J Toatley
*Assistant Examiner* — Iyabo S Alli
(74) *Attorney, Agent, or Firm* — Wood, Herron & Evans, LLP

(57) ABSTRACT

An optical sensor (10) for fitting to a washing machine or dishwasher is proposed, comprising: a housing (16), an arrangement, which is housed in the housing, of optical components, the optical components comprising a controllable light emitter (26) and a first and a second light receiver (28, 30), and an electronic analysis and control unit (36) which is connected to the light emitter (26) and the two light receivers (28, 30), the first light receiver (28) being arranged at the end of a first light measurement path (54) which starts at the light emitter (26) and runs on a portion outside the housing (16), and the second light receiver (30) being arranged at the end of a second light measurement path (56) which starts at the light emitter (26), and when the sensor is fitted to the machine as specified, the first light measurement path running on a portion through a washing space (14) of the machine, and is the second light measurement path running completely outside this washing space, the analysis and control unit (36) being set up to control the luminous flux of the light emitter (26), depending on an output signal of the second light receiver (30).

12 Claims, 1 Drawing Sheet

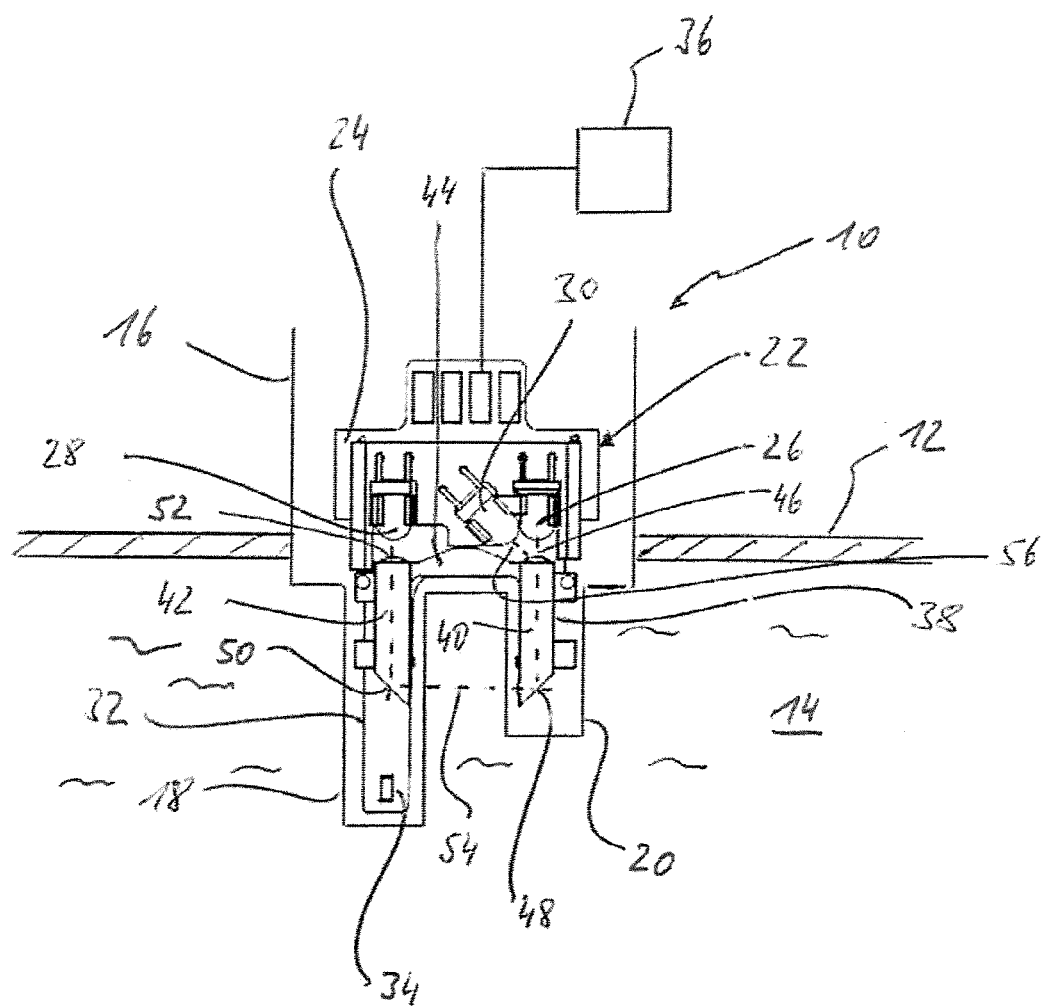

OPTICAL SENSOR FOR MOUNTING TO A WASHING MACHINE OR DISH WASHER

The present disclosure concerns an optical sensor, which is intended for fitting to a washing machine or dishwasher, the washing machine or dishwasher being preferably intended for the domestic sector or catering sector.

Optical sensors of the kind considered here can be used, in particular, as turbidity sensors, with which, in a washing machine or dishwasher, the turbidity of the washing water can be determined. From the turbidity, conclusions about the degree of dirtiness of the clothes or dishes to be washed can be drawn. To be able to measure the turbidity of the washing water, part of a light measurement path defined by the sensor runs outside the sensor, through a washing space, which is rinsed by the washing water, of the relevant machine. Light which is radiated by the sensor along this light measurement path undergoes attenuation, depending on the turbidity of the washing water, on the part of the light measurement path which runs outside the sensor through the washing space.

The term washing water here represents any washing liquids which are used for washing clothes or dishes. The washing liquid includes water as its main component, and can include various additions, e.g. cleansing substances, fabric softeners or other additives.

Regarding the prior art concerning optical sensors which can be used as turbidity sensors, reference is made to WO 2006/050767 A2, for example.

Traditional turbidity sensors usually have a light-emitting diode (LED) as the light emitter and a photodiode as the light receiver. Such diodes are semiconductor elements, which usually have a temperature dependency of their photoelectrical properties. For example, in the case of many LEDs, a reduction of the radiated luminous power with increasing temperature can be observed. In reverse, in the case of photodiodes an increase of sensitivity with increasing temperature can often be observed. In general, it cannot be assumed that the decreasing luminous power on the emitter side and the increasing sensitivity on the receiver side compensate completely for each other. The sensor as a whole therefore often has a temperature dependency of the sensor output signal.

This temperature dependency is a problem in that in the case of washing machines and dishwashers of the kind considered here, the temperature of the washing water, i.e. the ambient temperature acting on the opto-electrical components of the sensor, can vary relatively strongly during a cleansing cycle. For example, the temperature at the start of the cleansing cycle can correspond approximately to the normal temperature (e.g. 20° C.), and during the cleansing cycle it can rise to 60° C. or above. Simply because of this temperature rise, the output signal of the sensor changes. Additionally, during the cleansing cycle, the turbidity of the washing water changes, which also results in a change of the output signal of the sensor. Both effects, i.e. temperature increase and change of turbidity, therefore affect the sensor output signal. However, with the turbidity sensor only the turbidity of the washing water should be measured, so that the temperature effect is a disturbance variable, and a possible way of compensating for it should be sought.

An object of the invention is to provide an optical sensor which is suitable for use as a turbidity sensor, with temperature-compensating properties.

To achieve this object, the invention provides an optical sensor for fitting to a washing machine or dishwasher, comprising
    a housing,
    an arrangement, which is housed in the housing, of optical components, the optical components comprising a controllable light emitter and a first and a second light receiver, and
    an electronic analysis and control unit which is connected to the light emitter and the two light receivers,
the first light receiver being arranged at the end of a first light measurement path which starts at the light emitter and runs on a portion outside the housing, and the second light receiver being arranged at the end of a second light measurement path which starts at the light emitter, and when the sensor is fitted to the machine as specified, the first light measurement path running on a portion through a washing space of the machine, and the second light measurement path running completely outside this washing space. The analysis and control unit is set up to control the luminous flux of the light emitter, depending at least on an output signal of the second light receiver.

In the case of the solution according to the invention, part of the light radiated by the light emitter can be used to generate, by means of the second light receiver, a reference signal which is monitored by the analysis and control unit. The relevant part of the light of the light emitter runs along the second light measurement path, which does not run through the washing space which is rinsed by the washing liquid of the machine, for which reason the light which runs along the second light measurement path is not affected by a medium of varying turbidity. Variations of the output signal, which acts as a reference signal, of the second light receiver can therefore be an indicator of a change of the ambient temperature of the sensor, e.g. of an increase of the temperature of the washing water. To compensate at least partially for such temperature effects in the output signal of the first light receiver, which receives a part of the light of the light emitter which has been passed through the washing space and thus affected by the turbidity of the washing water, the analysis and control unit can control the luminous flux of the light emitter depending on the output signal of the second light receiver. For this purpose, the analysis and control unit can preferably control an electrical feed current which is fed to the light emitter, or/and an electrical voltage applied to the light emitter. In the case of a LED which is used as a light emitter, the analysis and control unit can, for example, depending on the course over time of the output signal of the second light receiver, change the current flowing through the LED, to change in this way the strength of the light emitted by the diode.

In a preferred embodiment, the analysis and control unit is set up to control the luminous flux of the light emitter, in the sense of holding the output signal of the second light receiver constant. In this respect, the analysis and control unit can implement a regulating function, to hold the output signal of the second light receiver at a desired level. This level can, for example, be defined independently of the current cleansing cycle of the machine, or, for example, the output signal of the second light receiver can be measured at the start of a cleansing cycle by the analysis and control unit, and used as the setpoint value for the further course of the cleansing cycle. For a new cleansing cycle, this process can be repeated, so that in different cleansing cycles, different setpoint values for the output signal of the second light receiver may be used.

By controlling the luminous flux of the light emitter depending on the output signal of the second light receiver, fluctuations of the strength of the light radiated by the light emitter, caused by temperature-dependent or other effects (e.g. aging), are successfully compensated for. Temperature-dependent fluctuations of the sensitivity of the second light receiver are also successfully compensated for. A change of the sensitivity of the second light receiver (reference detector), like a change of the luminous flux which strikes the second light receiver, results in a change of the output signal of the second light receiver, and the analysis and control unit converts this change into a corresponding adjustment of the radiated luminous flux of the light emitter.

The resulting temperature dependency of the sensor output signal, which corresponds to or is derived from the output signal of the first light receiver (turbidity detector), corresponds to the difference between the temperature dependency of the sensitivity of the reference detector and the temperature dependency of the sensitivity of the turbidity detector. By choosing, for both detectors, components which at least nominally have the same temperature dependency of the sensitivity (or in general, of the photoelectrical properties), it is possible, also for the output signal of the sensor, to achieve the most complete temperature compensation. To be able to use components with nominally the same photoelectrical properties for both light receivers, it is useful to have the light emitter and the second light receiver (reference detector) as separate components. However, within the invention, structural integration of the light emitter and the second light receiver into a single semiconductor component should not be excluded in principle.

The first and second light measurement paths can run separately from each other over their whole lengths. For example, the light emitter can have a radiation characteristic with a major lobe and one or more minor lobes, the major lobe being radiated into the first light measurement path and one or more of the minor lobes being radiated into the second light measurement path. For example, the light emitter and the second light receiver can be arranged relative to each other in such a way that the second light receiver can receive the relevant minor lobe(s) directly, without other optical elements (e.g. reflective surfaces, lenses or similar) being connected between them.

In an alternative version, the first and second light measurement paths can partly coincide, i.e. take a common route along a part of their length. For example, in the first light measurement path an optical element which decouples a part from the light which the light emitter emits into the first light measurement path can be arranged, the decoupled part going on to the second light measurement path, and the part which has not been decoupled remaining on the first light measurement path. For example, such light decoupling can be achieved with a converging lens, into which at least part of the light radiated by the light emitter (e.g. a major lobe) is radiated to generate a collimated light beam. On the converging lens, unavoidable reflections occur, it being possible to guide the reflected light or at least part of it onto the second light receiver.

In a preferred version, the optical components of the sensor also include a light guiding structure made of a transparent material, with a light entry point, a plurality of reflective surfaces for a light beam which is guided within the light guiding structure, and a light exit point, the light entry point, the reflective surfaces and the light exit point lying in the first light measurement path, and that portion of the first light measurement path which runs outside the housing lying between a pair of the reflective surfaces. The light which reaches the second light receiver can thus be decoupled from a light beam, which comes from the light emitter and strikes the light entry point of the light guiding structure, by reflection at or in the light guiding structure.

The invention is further explained below on the basis of the attached FIG. 1. This shows an embodiment of an optical sensor 10, which is used as a turbidity sensor, in a fitted situation in a washing machine or dishwasher. The sensor 10 is inserted into is a mounting opening of a limiting wall 12 of a washing space 14, which is rinsed by the washing water which is used to wash the clothes or dishes. It is used to measure the turbidity (the degree of dirtiness) of the washing water. For this purpose, it radiates light along a measurement path, which runs through the washing space 14 for part of its length. On this portion, the light undergoes attenuation, depending on the degree of dirtiness of the washing water, it being possible to deduce the degree of dirtiness of the good to be washed from the degree of attenuation.

The sensor 10 has a schematically indicated housing 16 with multiple (here two) longitudinal protuberances 18, 20 which extend into the washing space 14. In the housing 16, an electronic module 22 with a circuit board 24 is received, and a LED 26 which is used as a light emitter, a photodiode 28 which is used as a turbidity detector, and a further photodiode 30 which is used as a reference detector, are attached to it. The photodiode 28 forms a first light receiver in the meaning of the invention, and the photodiode 30 forms a second light receiver. The circuit board 24 has an arm 32 which extends into the protuberance 18, and to which a temperature sensor 34 to capture the temperature of the washing water is attached. Instead of the photodiodes 28, 30, any other photosensitive components such as phototransistors can be used for the reference detector and turbidity detector.

An electronic analysis and control unit 36 captures the electrical measurement signals which are supplied by the two photodiodes 28, 30 and the temperature sensor 34. The analysis and control unit 36 can, for example, include a microprocessor, which can be on a separate printed circuit board outside the sensor housing 16. However, it is also conceivable that the electrical and/or electronic components of the analysis and control unit 36 are arranged at least partly, or even completely, on the circuit board 24. The analysis and control unit 36 is shown in FIG. 1 outside the circuit board 24 only for better clarity, and this implies no restriction of the concrete position of this unit in relation to the circuit board 24.

The optical components which are housed in the sensor housing 16 include, in addition to the diodes 26, 28, 30, a light guiding structure 38 which is made of a highly transparent plastic, and which includes two longitudinal light guiding bodies (light guiding fingers) 40, 42 which each extend into one of the housing protuberances 18, 20. In the shown exemplary case, the two light guiding bodies 40, 42 are joined continuously in one piece by a bridge part 44. The light guiding body 40 forms, at a place facing the LED 26, a converging lens 46, which is used as the light entry point for the light coming from the LED 26. The converging lens 46 causes collimation of the usually divergent light beam coming from the LED 26, so that within the light guiding body 40, an essentially parallel light beam runs. At its free end extending into the protuberance 20, the light guiding body 40 forms a reflective surface 48, at which the parallel light beam which runs in the light guiding body 40 in the direction of the other light guiding body 42 is reflected. The reflection at the reflective surface 48 can, for example, be based on total reflection. Alternatively, implementing the reflective surface 48 in metallised form is conceivable.

The light beam which is reflected at the reflective surface 48 leaves the housing 16 and passes through a part of the washing space 14 between the two housing protuberances 18, 20, before, at the protuberance 18, it re-enters the housing 16 and from there enters the light guiding body 42. The light guiding body 42 forms a reflective surface 50, at which the light beam is reflected, and runs from there in the light guiding body 42 as far as a converging lens 52, at which the light beam leaves the light guiding structure 38 and reaches the turbidity detector 28. The converging lens 52 forms a light exit point, at which the light finally leaves the light guiding structure 38. The route which the light takes from the LED 26 to the photodiode 28 through the light guiding structure 38 forms a first light measurement path in the meaning of the invention. This light measurement path is indicated in FIG. 1 by a dashed line at 54.

The reflection of the light which runs along the first light measurement path 54 at the reflective surface 50 can—just as in the case of the reflective surface 48—be based on total reflection or on a metallised implementation of this surface.

In the shown example, the photodiode 30 is arranged directly adjacently to the LED 26. It detects part of the light radiated by the LED 26. This part can, for example, be such a part which is not radiated into the light guiding body 40. For example, it is conceivable that at the converging lens 46 only one major lobe (or a part of such a major lobe) of the light radiated by the LED 26 is coupled into the light guiding body 40, and one or more minor lobes (if they exist) are not captured by the converging lens 46. The photodiode 30 can then be arranged on the circuit board 24 in such a way that it is irradiated directly by such a minor lobe of the LED 26. Alternatively, it is conceivable that the light which the photodiode 30 detects is at least partly derived from a light beam which strikes the converging lens 46 starting from the LED 26. For example, light which is reflected at the converging lens 46 can be captured by the photodiode 30, or light which is reflected at another place of the light guiding structure 38 can be captured by the photodiode 30. It is understood that the light detected by the photodiode 30 can also be derived at least partly from reflections at the housing 16.

The distance which the light detected by the photodiode 30 travels starting at the LED 26 is a second light measurement path in the meaning of the invention. This second light measurement path can coincide with the first light measurement path 54 on part of its length. This is the case, for example, if the photodiode 30 detects light which is reflected at the converging lens 46. The route between the LED 26 and the converging lens 46 is then a common part of both light measurement paths. The course of the second light measurement path in the case of such a reflection at the converging lens 46 is shown in FIG. 1 by a dashed line at 56.

The three diodes 26, 28, 30 are semiconductor elements which can show temperature dependency of their electro-optical properties. For example, the LED 26 can have a luminosity which falls with increasing temperature, whereas the two photodiodes 28, 30 have higher sensitivity with increasing temperature. The change of luminosity or sensitivity depending on temperature can, for example, be expressed by a temperature coefficient, which indicates a percentage change per degree Kelvin. To give a numerical example, which of course is not intended to be in any way restrictive, the luminous intensity of the LED 26 in the temperature range (usually starting at about 20° C. and going up to about 90° C. for boil wash) which is relevant to operation of the washing machine or dishwasher can have a temperature coefficient of −0.6%/K. In contrast, for example, the sensitivity of the turbidity detector 28 in this temperature range can have a temperature coefficient of −0.3%/K. Since the two temperature dependencies are superimposed, the output signal of the turbidity detector 28 in the case of a temperature increase of 33° C. would fall by about 10%. It is problematical here that this fall depends purely on temperature, without anything having to change regarding the turbidity of the washing water. However, if nothing else is done the analysis and control unit 36 cannot detect whether a change of the output signal of the turbidity detector 28 is caused by temperature or turbidity.

It is also understood that the temperature dependency of the diodes does not have to be constant, but can be changeable in different temperature regions. Additionally, in the case of the LED 26, the temperature dependency can depend on the magnitude of the electric current which flows through it.

The reference detector 30 is used for temperature compensation of the sensor 10. Usefully for this purpose, for the reference detector a photodiode of the same type and nominally equal electro-optical properties (in particular, equal temperature coefficients) as for the turbidity detector 28 is used. To remain with the above numerical example, therefore, for the reference detector 30 a photodiode of which the sensitivity also has a temperature coefficient of +0.3%/K is preferably used. Of course, within the invention using photodiodes of different types for the detectors 28, 30 is not excluded, but the result may be a compensation effect which is not optimal.

For temperature compensation of the sensor 10, the analysis and control unit 36 analyses the detector signal (output signal) of the reference detector 30, and monitors it for changes. After the second light measurement path 56 does not leave the housing 16 and therefore does not run through the washing space 14, the luminous flux which arrives at the reference detector 30 is independent of the turbidity of the washing water. Changes of the water turbidity therefore have no effect on the output signal of the reference detector 30. In contrast, temperature changes of the washing water can affect the output signal of the reference detector 30, that is above all if a luminosity of the LED 26 which reduces at higher temperatures is not completely compensated for by a sensitivity of the reference detector 30 which increases at higher temperatures, in other words if the sum of the temperature coefficients of the LED 26 and of the reference detector 30 differs from zero. In this case, the analysis and control unit 36 can ascertain a change of the output signal of the reference detector 30 at changing temperatures. By suitable regulating means, which can be implemented in software or/and hardware, the analysis and control unit 36 can control the LED 26 so that the output signal of the reference detector 30 always remains essentially constant. For this purpose, the analysis and control unit 36 can, for example, control the current flowing through the LED 26, and thus cause a change of its luminous flux. It is understood that the electric current flowing through the LED 26 can additionally be controlled depending on one or more further parameters.

By such regulation of the output signal of the reference detector 30 to a given constant value, the temperature effect on the output signal of the sensor 10, i.e. the output signal of the turbidity detector 28, can be reduced or even eliminated to a very large extent. Optimal compensation is possible if the sensitivities of both detectors 28, 30 have the same temperature behaviour. If the detectors 28, 30 have different temperature dependencies, the resulting temperature dependency of the sensor output signal corresponds to the difference of the temperature dependencies of the two detectors 28, 30.

The target value to which the output signal of the reference detector 30 is regulated is can be, for example, defined depending on the temperature which is measured by means of the temperature sensor 34. For this purpose, it is conceivable that in the analysis and control unit 36, different target values for different washing water temperatures are stored in advance in tables.

Where this disclosure mentions that the second light measurement path runs completely outside the washing space, this should be understood, in particular, as meaning that the second light measurement path does not run through an area which is rinsed by the washing water of the washing machine or dishwasher, so that the intensity of the light which runs along the second light measurement path is not affected by the water turbidity. Regarding the embodiment according to FIG. 1, it is not necessary for this purpose that the second light measurement path 56 runs completely beyond the limiting wall 12 in the dry area of the machine. Instead, it is quite possible that the second light measurement path runs at least partly on the washing space 14 side of the limiting wall 12, but there does not escape from the sensor 10 into the areas of the washing space 14 which are rinsed by liquid.

The invention claimed is:

1. An optical sensor for fitting to a washing machine or dishwasher including a washing space, the optical sensor comprising:
   a housing,
   an arrangement of optical components located in the housing, the optical components comprising a controllable light emitter and first and second light receivers configured to receive a light beam from the light emitter and produce a corresponding electrical output signal, and
   an analysis and control unit which is connected to the light emitter and the two light receivers, the analysis and control unit controlling the luminous flux of the light emitter depending at least on the output signal of the second light receiver,
   the first light receiver being arranged at the end of a first light measurement path which starts at the light emitter and runs on a portion outside the housing and through the washing space, and
   the second light receiver being arranged at the end of a second light measurement path which starts at the light emitter and runs in the housing and completely outside the washing space, the second light measurement path also including at least one optical surface that reflects light propagating along the second light measurement path such that the second light measurement path is not defined by a direct line between the light emitter and the second light receiver.

2. The optical sensor according to claim 1, wherein the analysis and control unit controls the luminous flux of the light emitter so as to hold the output signal of the second light receiver constant.

3. The optical sensor according to claim 1, wherein the analysis and control unit controls the luminous flux of the light emitter by controlling an electrical feed current which is fed to the light emitter, and/or an electrical voltage which is applied to the light emitter.

4. The optical sensor according to claim 1, wherein the light emitter and the second light receiver are separate components.

5. The optical sensor according to claim 4, wherein the first light receiver and the second light receiver are separate components with nominally equal electro-optical properties.

6. The optical sensor according to claim 1, wherein the first and second light measurement paths run completely separately from each other.

7. The optical sensor according to claim 1, wherein the first and second light measurement paths partly coincide.

8. The optical sensor according to claim 1, wherein the optical components of the sensor also include a light guiding structure made of a transparent material, with a light entry point, a plurality of reflective surfaces for a light beam which is guided within the light guiding structure, and a light exit point, wherein the light entry point, the reflective surfaces and the light exit point lie along the first light measurement path, and that portion of the first light measurement path which runs outside the housing extends between a pair of the reflective surfaces.

9. The optical sensor according to claim 8, wherein the light guiding structure includes first and second longitudinal protuberances extending into the washing space from the housing, and the optical sensor further comprises:
   a temperature sensor positioned within one of the first and second longitudinal protuberances and operatively coupled to the analysis and control unit such that the analysis and control unit controls the luminous flux of the light emitter depending on a temperature sensed within the washing space by the temperature sensor.

10. The optical sensor according to claim 9, further comprising:
   a first converging lens located at the light entry point of the light guiding structure and including the at least one optical surface, wherein the first converging lens collimates a first portion of light emitted from the light emitter and transmits this first portion of light as a light beam along the first light measurement path, and the first converging lens reflects a second portion of light emitted from the light emitter toward the second light receiver along the second light measurement path.

11. The optical sensor according to claim 10, further comprising:
   a second converging lens located at the light exit point of the light guiding structure, the second converging lens collimating the light beam traveling along the first light measurement path and directing the light beam toward the first light receiver.

12. The optical sensor according to claim 1, further comprising:
   a first converging lens including the at least one optical surface, wherein the first converging lens collimates a first portion of light emitted from the light emitter and transmits this first portion of light as a light beam along the first light measurement path, and the first converging lens reflects a second portion of light emitted from the light emitter toward the second light receiver along the second light measurement path.

* * * * *